US00RE39050E

(19) United States
(12) Reissued Patent
Draper et al.

(10) Patent Number: US RE39,050 E
(45) Date of Reissued Patent: Mar. 28, 2006

(54) METHODS OF USE FOR INHIBITING BONE LOSS AND LOWERING SERUM CHOLESTEROL

(75) Inventors: Michael W. Draper, Carmel, IN (US); Larry J. Black, Franklin, IN (US)

(73) Assignee: Eli Lilly and Company, Indianapolis, IN (US)

(21) Appl. No.: 10/375,274

(22) Filed: Feb. 27, 2003

Related U.S. Patent Documents

Reissue of:
(64) Patent No.: 5,478,847
Issued: Dec. 26, 1995
Appl. No.: 08/205,012
Filed: Mar. 2, 1994

(51) Int. Cl.
*A01N 43/12* (2006.01)

(52) U.S. Cl. ..... 514/443
(58) Field of Classification Search ..... 514/333, 514/422, 578, 443, 448
See application file for complete search history.

(56) References Cited

U.S. PATENT DOCUMENTS

| | | | | | |
|---|---|---|---|---|---|
| 4,133,814 | A | * | 1/1979 | Jones et al. | 548/525 |
| 4,185,108 | A | | 1/1980 | Samour et al. | |
| 4,380,635 | A | * | 4/1983 | Peters | 546/202 |
| 4,418,068 | A | * | 11/1983 | Jones | 514/337 |
| 4,729,999 | A | | 3/1988 | Young | |
| 4,894,373 | A | | 1/1990 | Young | |
| 4,970,237 | A | | 11/1990 | Jensen et al. | |
| 5,011,853 | A | | 4/1991 | Olney | |
| 5,075,321 | A | | 12/1991 | Schreiber | |
| 5,118,667 | A | | 6/1992 | Adams | |
| 5,208,031 | A | | 5/1993 | Kelly | |
| 5,393,763 | A | * | 2/1995 | Black et al. | 514/333 |
| 5,395,842 | A | | 3/1995 | Labrie et al. | |
| 5,441,947 | A | | 8/1995 | Dodge et al. | |
| 5,445,941 | A | | 8/1995 | Yang | |
| 5,457,116 | A | | 10/1995 | Black et al. | |
| 5,457,117 | A | | 10/1995 | Black et al. | |
| 5,461,065 | A | | 10/1995 | Black et al. | |
| 5,462,949 | A | | 10/1995 | Jones et al. | |
| 5,464,845 | A | | 11/1995 | Black et al. | |
| 5,468,773 | A | | 11/1995 | Dodge et al. | |
| 5,472,962 | A | | 12/1995 | Koizumi et al. | |
| 5,482,949 | A | | 1/1996 | Black et al. | |
| 5,510,370 | A | | 4/1996 | Hock | |
| 5,534,527 | A | | 7/1996 | Black et al. | |
| 5,567,713 | A | | 10/1996 | Cullinan et al. | |
| 5,591,753 | A | | 1/1997 | Black et al. | |
| 5,610,168 | A | | 3/1997 | Draper | |
| 5,624,940 | A | | 4/1997 | Bryant et al. | |
| 5,629,425 | A | | 5/1997 | LaBell et al. | |
| 5,641,790 | A | | 6/1997 | Draper | |
| 5,646,137 | A | | 7/1997 | Black et al. | |
| 5,731,327 | A | | 3/1998 | Luke | |
| 5,747,510 | A | | 5/1998 | Draper | |
| 5,811,120 | A | | 9/1998 | Gibson et al. | |
| 5,972,383 | A | | 10/1999 | Gibson et al. | |
| 6,087,378 | A | | 7/2000 | Cullinan et al. | |
| 6,096,781 | A | | 8/2000 | Cullinan | |
| 6,156,786 | A | | 12/2000 | Cullinan | |
| 6,395,769 | B1 | | 5/2002 | Cullinan | |
| 6,458,811 | B1 | | 10/2002 | Arbuthnot et al. | |
| 6,713,494 | B1 | | 3/2004 | Cuff et al. | |
| 2003/0212058 | A1 | | 11/2003 | Black et al. | |

FOREIGN PATENT DOCUMENTS

| | | | | |
|---|---|---|---|---|
| AU | 4422193 | A1 | | 2/1994 |
| BR | 9303013 | A | | 2/1994 |
| CA | 2101356 | A | | 1/1994 |
| EP | 0062505 | | | 10/1982 |
| EP | 0068563 | | | 1/1983 |
| EP | 0584952 | | | 3/1994 |
| EP | 0605193 | | | 7/1994 |
| EP | 0674903 | | | 10/1995 |
| GB | 2097788 | | | 11/1982 |
| HU | 9302163 | A0 | | 7/1994 |
| IL | 0106450 | A0 | | 11/1993 |
| NO | 303863 | | | 1/1994 |
| NO | 304924 | | | 6/1994 |
| PL | 177348 | | | 2/1994 |
| WO | WO93/10113 | | * | 5/1993 |
| WO | WO 93/10113 | | | 5/1993 |
| WO | WO93/1074 | | * | 6/1993 |
| ZA | 9305283 | | | 1/1994 |

OTHER PUBLICATIONS

Black et al., "Distinct, Structure–Related Profiles of Estrogenic and Anti–Estrogenic Activity in the Tamoxifen and LY117018 Series;" The Endocrine Society, Abstract 1982.*
Black et al., "Uterine Bioassay of Tamoxifen, Trioxifene, and New Estrogen Antagonist (LY117018) in Rats and Mice," Life Sciences, 26:1980, 1453–1458.*
Black et al., "Differential Interaction of Antiestrogens with Cytosol Estrogen Receptors," Molecular and Cellular Endocrinology, 22:1981, 95–103.*

(Continued)

*Primary Examiner*—Edward J. Webman
(74) *Attorney, Agent, or Firm*—Woodard, Emhardt, Moriarity, McNett & Henry LLP

(57) ABSTRACT

A method of inhibiting bone loss or resorption, or lowering serum cholesterol, comprising administering to a human in need thereof a compound having the formula (I)

or a pharmaceutically acceptable salt or solvate thereof, in a low dosage amount. Also encompassed by the invention is a a pharmaceutical formulation in unit dosage form comprising, per unit dosage, a low dosage amount.

10 Claims, No Drawings

OTHER PUBLICATIONS

Black et al., "Evidence for Biological Action of the Antiestrogens LY117018 and Tamoxifen by Different Mechanisms," Endocrinology 109; 1981, 987–989.*

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.*

Black et al., Synthesis and Antiestrogenic Activity of [3,4–Dihydro–2(4–methoxypehnyl)–1–napthalenyl][4–[2–pyrrolidinyl)ethoxyl]–phenyl] methanone, methanesulfonic acid salt, Journal of Medicinal Chemistry 22; 1979, 962–966.*

Bryant et al., "Raloxifene is a Tissue Specific Estrogen Agonist", Am Soc. Bone & Min. Res., Tampa, Sep. 18–22, 1993.*

Cypriani B, Tabacik C, Descomps B, Crastes DP A. Role of Estrogen Receptors and Antiestrogen Binding Sites in an Early Effect of Antiestrogens, The Inhibition of Cholesterol Biosynthesis. J. Steroid Biochem 1988;31(5):763–771.

Cypriani B, Tabacik C, Descomps B. Effect on Estradiol and Antiestrogens on Cholesterol Biosynthesis in Hormone–Dependent and Independent Breast Cancer Cell Lines. Biochim. Biophys. Acta, ser Mol. Cell Res 1988:972(2):167–178.

Copending U.S. Appl. No. 10/446,210, filed May 27, 2003, Black et al.

Jordan, VC, Estrogen Antiestrogen action and Breast Cancer Therapy, (excerpts) , pp. 28–30, and 516–517, Nov. 24, 1986.

Black, L. J. "Biological Actions and Binding Properties of a New Estrogen Antagosist LY117018," In: *Hormone Antagonists,* 129–45, 1982 (M. K. Agarwal ed.) Walter de Gruyter and Co., Berlin N.Y.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Tex., Jun. 8–10, 1983, abs. 93.

Williams, et al., Journal of Bone and Mineral Research, 6 (1991).

Copending U.S. Appl. No. 10/375,339, filed Feb. 27, 2003, Black.

Copending U.S. Appl. No. 10/375,341, filed Feb. 27, 2003, Black et al.

Barr's Paragraph IV Certification (pp. 1–29) and 2 page letter (Oct. 9, 2002) enclosing the same.

Eli Lilly and Company's Supplemental Response To Barr's Interrogatory No. 12 (served on Jun. 28, 2004).

Barr Laboratories' Second Supplemental Responses to Eli Lilly's Interrogatories Nos. 5, 6 and 9 (served on Sep. 20, 2004).

Banks PK, Meyer K, Brodie AM H. Regulation of ovarian steroid biosynthesis by estrogen during proestrus in the rat. Endocrinology 1991;129(3):1295–1304.

Beall, PT, Misra LK, Young RL, Spjut HJ, Evans HJ, Leblanc. Clomiphene Protects Against Osteoporosis in the Mature Ovariectomized Rat. Calcif. Tissue Int., 36: 123–125 (1984).

Black LJ, Masahiko S, Rowley ER, Magee DE, Bekele A, Williams DC, Cullinan GJ, Bendele R, Kauffman RF, Benach WR, Frolik CA, Tamine JD, Bryant HU. Raloxifene (LY139481 HCl) Prevents Bone Loss and Reduces Serum Cholesterol without Causing Uterine Hypertrophy in Ovariectomized Rats. J. Clin. Invest. Jan. 1994;93:63–69.

Buzdar AU, Marcus C, Holmes F, Hug V, Hortobagyi G. Phase II Evaluation of LY156758 in metastatic breast cancer. Oncology 1988;45(5):344–345.

Chou Y, Iguchi T, Bern H. Effects of antiestrogens on adult and neonatal mouse reproductive organs. Reprod Toxicol 1992;6(5):439–46.

Clemens JA, Bennett DR, Black LJ, Jones CD. Effects of a new antiestrogen, keoxifene (LY156758), on growth of carcinogen–induced mammary tumors and on LH and prolactin levels. Life Sci 1983;32(5):2869–2875.

Daniel CW, Silberstein GB, Strickland P. Direct action of 17beta–estradiol on mouse mammary ducts analyzed by sustained release implants and steroid autoradiography. Cancer Res 1987;47(22):6052–57.

De Launoit Y, Veilleux R, Dufour M, Simard J, Labrie F. Characteristics of the biphasic action of androgens and of the potent antioproliferative effects of the new pure antiestrogen EM–139 on cell cycle kinetic parameters in LNCaP human prostatic cancer cells. Cancer Res 1991;51(19):5165–5170.

Draper MW, Flowers DE, and Huster WJ. Effects of raloxifene (LY 139481) on biochemical markers of bone and lipid metabolism in healthy post–menopausal Women. Abstracts of the Fourth International Symposium on Osteoporosis , Hong Kong 1993.

Draper MW, Flowers DE, Huster WJ, and Neild JA. Effects of raloxifene (LY 139481 HCl) on biochemical markers of bone and lipid metabolism in healthy postmenopausal women. Proceedings from the Fourth International Symposium on Osteoporosis, Hong Kong, 1993.

Draper MW, Boss SM, Huster WJ, and Neild JA. Effects of Raloxifene Hydrochloride on Serum Markers of Bone and Lipid Metabolism—Dose–Response Relationships. Abstracts of The First International Conference on Steroids and Bone, Florence, Italy, May 1994, Calcified Tissue Int.54:329–362.

Feldman S, Minne HW, Parvizi S, Pfeifer M, Lempert UG, Bauss F et al. Antiestrogen and antiandrogen administration reduce bone mass in the rat. Bone and Mineral 1989;7(3):245–254.

Gabriel SM, Koenig JI, Washton DL. Estrogen stimulation of galnin gene expression and galanin–like immunoreactivity in the rat and its blockade by the estrogen antagonist keoxifene (LY156758). Regulatory Peptides, 45(1993):407–419.

Gierthy JF, Lincoln DW II, Roth KE, Bowser SS, Bennett JA, Bradley L and Dickerman HW. Estrogen–stimulation of postconfluent cell accumulation and foci formation of human MCF–7 breast cancer cells. J. Cell. Biochem 1991;45(2):177–187.

Gottardis MM, Jordan VC. Antitumor actions of keoxifene and tamoxifen in the n–nitrosomethylurea–induced rat mammary carcinoma model. Cancer Res 1987;47(15):4020–4024.

Gottardis MM, Richio ME, Satyaswaroop PG, Jordan VC. Effect of steroidal and nonsteroidal antiestrogens on the growth of a tamoxifen–stimulated human endometrial carcinoma (EnCa101) in athymic mice. Cancer Res 1990;50(11):3189–3192.

Gray JM, Ziemian L. Antiestrogen binding sites in brain and pituitary of ovariectomized rates. Brain Res 1992;578(1–2):55–60.

Guttinger HR, Herth G, Stocker S, Kafitz KW, Kallenbach M. Antioestrogen inhibits myelination in brains of juvenile Zebra finches. NeuroReport 1993; 4(8):1019–1022.

Hubert J–F, Vincent A, Labrie F. Estrogenic activity of phenol red in rat anterior pituitary cell in culture. Biochem. Biophys. Res. Commun. 1986;141(3):885–891.

Iguchi T, Tani N, Sato T, Fukatsu N, Ohta Y. Developmental changes in mouse placental cells from several stages of pregnancy in vivo and in vitro. Biol. Reprod 1993;48(1):188–196.

Jiang S–Y, Parker CJ, Jordan VC. A model to describe how a point mutation of the estrogen receptor alters the structure–function relationship of antiestrogens. Breast Cancer Research and Treatment 1993; 26:139–147.

Jordan VC, Gottardis MM. Tamoxifen–stimulated growth of human endometrial carcinoma. New York Acad. Sci 1991;622:439–446.

Jordan VC. Laboratory studies to develop general principles for the adjuvant treatment of breast cancer with antiestrogens: problems and potential for future clinical applications. Breast Cancer Res. Treat 1983;3(Suppl.):73–86.

Jordan, VC, Phelps E, Lindgren, JU. Effects of anti–estrogens on bone in castrated and intact female rats. Breast Cancer Res. and Treat 1987;10:31–35.

Katz, J, Finlay, TH, Banerjee S, Levitz M. An Estrogen–Dependent Esterase Activity in MCF–7 Cells. J. Steroid Biochem. 1987;vol. 26, No. 6:687–692.

Kessel B, Hsueh AJW. Keoxifene (LY 156758) inhibits follicle–stimulating hormone induced differentiation of cultured rat granulosa cells. Life Sci 1987;40(11):1089–1097.

Kleinberg DL, Todd J, Babitsky G. Inhibition by estradiol of the lactogenic effect of prolactin in primate mammary tissue: reversal by antiestrogens LY 156758 and tamoxifen. Proc. Natl Acad. Sci. U.S.A. 1982;80:4144–4148.

Knecht M, Brodie AM H., Catt KJ. Aromatase inhibitors prevent granulosa cell differentiation: an obligatory role for estrogens in luteinizing hormone receptor expression. Endocrinology 1985;117(3):1156–1161.

Knecht M, Tsai–Morris CH, Catt KJ. Estrogen Dependence of Luteinizing Hormone Receptor Expression in Cultured Rat Granulosa Cells. Inhibition of Granulosa Cell Development by the Antiestrogens Tamoxifen and Keoxifene. Endocrinology 1985;16:1771–1777.

Labrie F, Poulin R, Simard J, Zhao HF, Labrie C, Dauvois S et al. Interactions between estrogens, androgens, progestine, and glucocorticoids in ZR–75–1 human breast cancer cells. Ann. New York Acad. Sci 1990;595:130–148.

Labrie F, Simard J, Poulin R, Hatton A–C, Labrie C, Dauvois S et al. Potent antagonism between estrogens and androgens on GCDFP–15 expression and cell growth in the ZR–75–1 human breast cancer cells. Ann. New York Acad. Sci 1990;586:174–187.

Liehr JG, Folse DS, Roy D. Lack of effectiveness of antiestrogens RU 39,411 or keoxifen in the prevention of estrogen–induced tumors in Syrian hamsters. Cancer Lett 1992;64(1):23–29.

Lilly's novel approach to osteoporosis. PJB Publications, Ltd. 1993.

Lindstrom TD, Whitaker NG, Whitaker GW. Disposition and metabolism of a new benzothiophene antiestrogen in rats, dogs and monkeys. Xenobiotica 1984;14(11):841–847.

Love et al. Effects of Tamoxifen on Bone Mineral Density in Postmenopausal Women with Breast Cancer. New England Journal of Medicine Mar. 26, 1992;326(13):852–856.

Luthy IA, Begin D, Labrie F. Mediation by the androgen receptor of the stimulatory and antiandrogenic actions of 17β–estradiol on the growth of androgen–sensitive shionogi mammary carcinoma cells in culture. Endocrinology 1988;123(3):1418–1424.

Mariotti A, Durham J, Frederickson R, Miller R, Butcher F, Mawhinney M. Actions and interactions of estradiol and retinoic acid in mouse anterior prostate gland. Biol. Reprod 1987;37(4):1023–1035.

Martinoli MG, Veilleux R, Pelletier G. Effects of triiodothyronine, dexamethasone and estradiol–17β on GH mRNA in rat pituitary cells in culture as revealed by in situ hybridization. Acta Endocrinol 1991;124(1):83–90.

McArdle CA, Schomerus E, Groner I, Poch A. Estradiol regulates gonadotropin–releasing hormone receptor number, growth and inositol phosphate production in αT3–1 cells. Mol. Cell. Endocrinol 1992;87(1–3):95–103.

Meisel RL, Dohanich GP, McEwen BS, Pfaff DW. Antagonim of sexual behavior in female rats by ventromedial hypothalamic implants of antiestrogen. Neuroendocrinology 1987;45(3):201–207.

Moon LY, Wakley GK, Turner, RT. Dose–Dependent Effects of Tamoxifen on Long Bones in Growing Rats: Influence of Ovarian Status. Endocrinology, 1991; vol. 129, No. 3, pp. 1568–1574.

Neubauer BL, Best KL, Clemens JA, Gates CA, Goode RL, Jones CD, Laughlin ME, Shaar CJ, Toomey RE, Hoover DM. Endocrine and Antiprostatic Effects of Raloxifene (LY156758) in the Male Rat. The Prostate 1993; 23:245–262.

Neubauer BL, Biser P, Jones CD, Mariotti A, Hoover DM, Thornton T et al. Antagonism of androgen and estrogen effects of guinea–pig seminal vesicle epithelium and fibromuscular stroma by keoxifene LY 156758. The Prostate 1989;15(3):273–286.

Ortmann O, Emons G, Knuppen R, Catt KJ. Inhibitory actions of keoxifene on luteinizing hormone secretion in pituitary gonadotrophs. Endocrinology 1988;123(2):962–968.

Ortmann O, Sturm R, Knuppen R, Emons G. Weak estrogenic activity of phenol red in the pituitary gonadotroph: re–evaluation of estrogen and antiestrogen effects. J. Steroid Biochem 1990;35(1):17–22.

Osborne CK, Hobbs K, Clark GM. Effect of estrogens and antiestrogens on growth of human breast cancer cells in athymic nude mice. Cancer Res 1985;45(2):584–590.

Peterson SL, Barraclough CA. Suppression of spontaneous LH surges in estrogen–treated overiectomized rats by microimplants of antiestrogens into the preoptic brain. Brain Res 1989;484(1–2):279–289.

Pini P. Bones of Contention. The Lancet, vol. 341:Apr. 10, 1993, pp. 950–951.

Poulin R, Baker D, Labrie F. Androgens inhibit basal and estrogen–induced cell proliferation in the ZR–75–1 human breast cancer cell line. Breast Cancer Res. Treat 1988;12(2):213–225.

Poulin R, Labrie F. Stimulation of cell proliferation and estrogenic response by adrenal $C_{19}$–$\Delta^5$–steroids in the ZR–75–1 human breast cancer cell line. Cancer Res 1986;46(10):4933–4937.

Poulin R, Merand Y, Poirier D, Levesque C, Dufour J–M, Labrie F. Antiestrogenic properties of keoxifene, trans–4–hydroxytamoxifen, and ICI 164384, a new steroidal antiestrogen, in ZR–75–1 human breast cancer cells. Breast Cancer Res. Treat 1989;14(1):65–76.

Richards J, Imagawa W, Balakrishnan A, Edery M, Nandi S. The lack of effect of phenol red or estradiol on the growth response of human, rat, and mouse mammary cells in primary culture. Endocrinology 1988;123(3):1335–1340.

Sanders M, Levinson Al, Schreiber AD. Hormonal modulation of macrophage clearance of IgG sensitized cells. Clin Res 1987;35(3):268–275.

Sikes, RA, Thomsen S, Petrow W, Neubauer BL, Chung LWK. Inhibition of Experimentally Induced Mouse Prostatic Hyperplasia by Castration or Steroid Antagonist Administration. Biology of Reproduction 1990;43:353–362.

Simard J, Labrie F. Adrenal $C_{19}$–5–ene steroids induce full estrogenic responses in rat pituitary gonadrotrophs. J Steroid Biochem 1987;26(5):539–546.

Simard J, Labrie F. Keoxifene shows pure antiestrogenic activity in pituitary gonadotrophs. Mol. Cell. Endocrinol. 1985;39:141–144.

Snyder BW, Beecham GD, Winneker RC. Studies on the mechanism of action of danazol and gestrinone (R2323) in the rat: evidence for a masked estrogen component. Fertil. Steril 1989;51(4):705–710.

Snyder BW, Beecham GD, Winneker RD. Danazol suppression of luteinizing hormone in the rat: evidence for mediation by both androgen and estrogen receptors. Proc. Soc. Exp. Biol. Med 1990;194(1):54–57.

Sundstrom SA, Komm BS, Xu Q, Boundy V, Lyttle RC. The stimulation of uterine complement component C3 gene expression by antiestrogens. Endocrinology 1990;126(3):1449–1456.

Tamoxifen Increases Spinal Bone Mineral Density in Postmenosausal Women. FDC Reports, T&G 11, Mar. 30, 1992.

Tamoxifen Trial Restricted, Scrip No. 1702, Mar. 20, 1992, p. 22.

Thomas T, Kiang DT. Additive growth–inhibitory effects of DL–α–difluoromethylornithine and antiestrogens on MCF–7 breast cancer cell line. Biochem. Biophys. Res. Commun 1987;148(3):1338–1345.

Tsai P–S, Hayes TB, Licht P. Role or Aromatization in Testosterone–Induced Inhibition of Luteinizing Hormone Secretion in Female Turtles, *Trachemys scripta.* Biology of Reporduction 1994(50):144–151.

Tsai P–S, Uchima F–D A., Hamamoto ST, Bern HA. Proliferation and differentiation of prepubertal mouse vaginal epithelial cells in vitro and the specificity of estrogen–induced growth retardation. In Vitro Cells. Dev. Biol 1991;27 A(6):461–468.

Turner et al. Tamoxifen Prevents the Skeletal Effects of Ovarian Hormone Deficiency in Rats. Journal of Bone and Mineral Research, 1987; 2(5):449–456.

Turner et al. Tamoxifen Inhibits Osteoclast–Mediated Resorption of Trabecular Bone in Ovarian Hormone–Deficient Rats. Endocrinology 1988;122(3):1146–1150.

Turner CH, Sato M, Bryant, HU. Raloxifene Preserves Bone Strength and Bone Mass in Overiectomized Rats. Endocrinology, 1994 vol. 135, No. 5, pp. 2001–2005.

Veldhuis JD, Azimi P, Juchter D, Garmey J. Mechanisms subserving the bipotential actions of estrogen on ovarian cells: studies with a selective anti–estrogen, LY 156758, and the sparingly metabolizable estrogen agonist, moxestrol. J. Steroid biochem 1986;24(5):977–982.

Veldhuis JD, Rodgers RJ, Furlanetto RW. Synergistic actions of estradiol and the insulin–like growth factor Somatomedin–C on swine ovarian (granulosa) cells. Endocrinology 1986;119(2):530–538.

Wakeling AE, Valcaccia B, Newboult E, Green LR. Non–steroidal antioestrogens–receptor binding and biological response in rat mammary carcinoma and human breast cancer cells. J. Steroid biochem 1984;20(1):111–120.

Wakeling AE, Valcaccia B. Antioestrogenic and antitumor activities of a series of non–steroidal antioestrogens. J. Endocrinol 1983;99(3):455–464.

Wakley GK and Turner RT. Sex Steroids and the Regulation of Bone Volume in the Rat. Cells & Material Supplement. 1991, vol. 1, pp. 85–91.

Welshons WV, Rottinghaus GE, Nonneman DJ, Dolan–Timpe M, Ross PF. A sensitive bioassay for detection of dietary estrogens in animal feeds. J. Vet. Diagn. Invest Oct. 1990;2(3):268–273.

Williams DC, Paul DC, and Black LJ. Effects of estrogen and tamoxifen on serum osteocalcin levels in ovariectomized rats. Bone and Mineral, 14 (1991):205–220.

Ammann, P., R. Rizzoli, D. Slosman, and J. P. Bonjour. 1992. Sequential and precise in vivo measurement of bone mineral density in rats using dual energy x–ray absorptiometry, *J. Bone Miner. Res.* 7:311–316.

Black, L. J., C. D. Jones, J. H. Clark, and J. A. Clemens. 1982. LY 156758: A unique anti–estrogen displaying high affinity for estrogen receptors, negligible estrogenic activity and near–total estrogen antagonism in vivo. *Breast Cancer Res. Treat.* 2:279.

Black LJ, Jones CD, Falcone JF. Antagonism of Estrogen Action with a New Benzothiophene Derived Antiestrogen. Life Sciences 1983;32:1031–1036.

Bryant, H.U., L.J. Black, E.R. Rowley, D.E. Magee, D.C. Williams, G.J. Cullinan, R.F. Kauffman, and M. Sato. Raloxifene (LY139481 HCI): Bone, lipid and uterine effects in the ovariectomized rat model. *J. Bone Miner. Res.* 8(Suppl. 1): S123, Aug. 1993; Program and Abstracts, Fifteenth Annual Meeting of the American Society for Bone & Mineral Research, Tampa, Florida, Sep. 18–22, 1993.

Bucolo, G., and H. David. 1973. Quantitative determination of serum triglycerides by the use of enzymes. *Clin. Chem.* 19:476–482.

Chao, Y., E. E. Windler, G. C. Chen, and R. J. Havel. 1979. Hepatic catabolism of rat and human lipoproteins in rats treated with 17–ά–ethinyl estradiol. *J. Biol. Chem.* 254:11360–11366.

Consensus Conference. Osteoporosis. 1984. *J. Am. Med. Assoc.* 252:799–802.

Cummings, S. R. 1991. Evaluating the benefits and risks of postmenopausal hormone therapy. *Am J. Med.* 91 (Suppl. 5B):14S–18S.

Dodge, J.A., M.G. Stocksdale, L.J. Black, E.R. Rowley, A. Bekele, H.W. Cole, C.E. Brown, D.E. Magee, G.A. Dehoney, and H.U. Bryant. Effects of steroidal and non–steroidal anti–estrogens in the ovariectomized rat. *J. Bone Miner. Res.* 8(Suppl. 1):S278, Aug. 1993; Program and Abstracts, Fifteenth Annual Meeting of the American Society for Bone & Mineral Research, Tampa, Florida, Sep. 18–22, 1993.

Donati, R. J., P. V. Harper, A. Hughes, and R. V. Hay. 1990. Serum cholesterol– and apoprotein B–lowing effects on cis–tamoxifen. *Arteriosclerosis.* 10:822A.

Evans, G., H. U. Bryant, M. Sato, and R. T. Turner. 1993. Raloxifene is a tissue specific estrogen agonist. *J. Bone Miner. Res.* 8(Suppl. 1):S134, Aug. 1993; Program and Abstracts, Fifteenth Annual Meeting of the American Society for Bone & Mineral Research, Tampa, Florida, Sep. 18–22, 1993.

Frolick et al., "In Vivo and In Vitro Metabolism of Raloxifene", *J. Bone Miner. Res.* 8(Suppl. 1):S282, Aug. 1993; Program and Abstracts, Fifteenth Annual Meeting of the American Society for Bone & Mineral Research, Tampa, Florida, Sep. 18–22, 1993.

Glasebrook et al., "Multiple Binding Sites for the Anti–estrogen Raloxifene", *J. Bone Miner. Res.* 8(Suppl. 1):S268, Aug. 1993; Program and Abstracts, Fifteenth Annual Meeting of the American Society for Bone & Mineral Research, Tampa, Florida, Sep. 18–22, 1993.

Gordon, T., W. B. Kannel, M.C. Hjortland, and P. M. McNamara. 1978. Menopause and coronary heart disease: The Framingham Study. *Ann. Int. Med.* 89:157–161.

Griffen, M. G., R. Kimble, W. Hopfer, and R. Pacifici. 1993. Dual energy x–ray absorptiometry of the rat: Accuracy, precision and measurement of bone loss. *J. Bone Miner. Res.* 8:795–800.

Henderson, B. E., R. K. Ross, and M. C. Pike. 1993. Hormonal chemoprevention of cancer in women. *Science (Wash. DC).* 259:633–638.

Hock et al., "Combination of Raloxifene and Human Parathyoid Hormone 1–34; Increased Femur Bone Mass in Young Ovariectomized (OVX) Rats", *J. Bone Miner. Res.* 8(Suppl. 1):S157, Aug. 1993; Program and Abstracts, Fifteenth Annual Meeting of the American Society for Bone & Mineral Research, Tampa, Florida, Sep. 18–22, 1993.

Jones, C. D., T. Suarez, E. H. Massey, L. J. Black, and F. C. Tinsley, 1979. Synthesis and anti–estrogenic activity of [3,4–dihydro–2–(4–methoxyphenyl)–1–napthalenyl][4–[2–pyrrolidinyl) ethoxy]–phenyl] methanone, methanesulfonic acid salt, *J. Med. Chem.* 22:962–966.

Jordan, V. C., K. E. Allen, and C. J. Dix. 1980. Pharmacology of tamoxifen in laboratory animals. *Cancer Treat. Rep.* 64:745–759.

Judd, H. L., D. R. Meldrum, L. J. Deftos and B. E. Henderson. 1983. Estrogen replacement therapy: Indications and complications. *Ann. Int. Med.* 98:195–205.

Kalu, D. N. 1991. The ovariectomized rat model of post–menopausal bone loss. *Bone Miner.* 15:175–192.

Kalu, D.N., C.C. Liu, E. Salerno, B. Hollis, R. Echon, and M. Ray. 1991. Skeletal response of ovariectomized rats to low and high doses of 17β–estradiol. *Bone Miner.* 14:175–187.

Kurl, R. N., and N. M. Borthwick. 1980. Clomiphene and tamoxifen action in the rat uterus. *J. Endocrinol.* 85:519–524.

Love, R. R., L. Cameron, B. L. Connell, and H. Leventhal. 1991. Symptoms associated with tamoxifen treatment in postmenopausal women. *Arch. Intern. Med.* 151:1842–1847.

Love, R. R., D. A. Wiebe, P. A. Newcomb, L. Cameron, H. Leventhal, V. C. Jordan, J. Feyzi, and D. L. DeMets. 1991. Effects of tamoxifen on cardiovascular risk factors in post–menopausal women. *Ann. Intern. Med.* 115:860–864.

Ma, P. T. S., T. Yamamoto, J. L. Goldstein, and M. S. Brown. 1986. Increased mRNA for low density lipoprotein receptor in livers of rabbits treated with 17–ά–ethinyl estradiol. *Proc. Natl. Acad. Sci. USA.* 83:792–796.

Matthews, K. A., E. Meilahn, L. H. Kuller, S. F. Kelsy, A. W. Cagguila, and R. R. Wing, 1989, Menopause and risk factors for coronary heart disease. *N. Engl. J. Med.* 321:641–646.

Overgaard, K., M. A. Hansen, S. B. Jensen, and C. Christiansen. 1992. Effect of salcatonin given intranasally on bone mass and fracture rates in established osteoporosis: A dose–response study. *Br. Med. J.* 305:556–561.

Riggs, B.L. 1991. Overview of osteoporosis. *West. J. Med.* 154:63–77.

Roudebush, R.E., D.E. Magee, D.N. Benslay, A.M. Bendele, and H.U. Bryant. 1993. Effect of weight manipulation on bone loss due to ovariectomy and the protective effects of estrogen in the rat. *Calcif. Tissue Int.* 53:61–64.

Sato et al., "DEXA Analysis of Raloxifene Effects on the Bones From Ovariectomized Rats," *J. Bone Miner. Res* 8(Suppl.1):S355, Aug. 1993; Program and Abstracts, Fifteenth Annual Meeting of the American Society for Bone & Mineral Research, Tampa, Florida, Sep. 18–22, 1993.

Staels, B., J. Auwerx, L. Chan, A. von Tol, M. Rosseneu, and G. Verhoeven. 1989. Influence of development, estrogens, and food intake on apolipoprotein A–I, A–II and E mRNA in rat liver and intestine. *J. Res.* 30:1137–1145.

Szego, C., and S. Roberts. 1953. Steroid action and interactions in uterine metabolism. *Recent Prog. Horm. Res.* 8:419–468.

Turner et al. Tamoxifen Inhibits Osteoclast–Mediated Resorption of Trabecular Bone in Ovarian Hormone–Deficient Rats. Endocrinology 1988; 122(3):1146–1150.

Turner, R. T., G. L. Evans, and G. K. Wakely. 1993. Mechanism of action of estrogen on cancellous bone balance in tibiae of ovariectomized growing rats: Inhibition of indices of formation and resorption. *J. Bone Miner. Res.* 8:359–366.

Walsh, B. W., I. Schiff, B. Rosner, L. Greenberg, V. Ravnikar, and F. M. Sacks. 1991. Effects of post–menopausal estrogen replacement on the concentrations and metabolism of plasma lipoproteins. *N. Engl. J. Med.* 325:1196–1204.

Wiebe, D. A., and J. T. Bernert. 1984. Influence of incomplete cholesterylester hydrolysis on enzymatic measurements of cholesterol. *Clin. Chem.* 30:352–356.

Windler, E. E. T., P. T. Kovanen, Y. Chao, M. S. Brown, R. J. Havel, and J. L. Goldstein. 1980. The estradiol–stimulated lipoprotein receptor of rat liver. *J. Biol. Chem.* 255:10464–10471.

Wronski, T. J., and C. F. Yen. 1991. The ovariectomized rat as an animal model for postmenopausal bone loss. *Cells Mater.* (Suppl. 1):69–74.

Wronski, T. J., C. F. Yen, K. W. Burton, R. C. Mehta, P. S. Newman, E. E. Soltis, and P. P. DeLuca. 1991. Skeletal effects of calcitonin in ovariectomized rats. *Endocrinology.* 129:2246–2250.

Wronski, T. J., M. Cintron, A. L. Doherty, and L. M. Dann. 1988. Estrogen treatment prevents osteopenia and depresses bone turnover in ovariectomized rats. *Endocrinology.* 123:681–686.

Yang et al., Raloxifene an Anti–Estrogen, Simulates the Effects of Estrogen in Inhibiting Bone Resorption Through Regulating TGFB–3 Expression in Bone. *J. Bone Miner. Res.* 8(Suppl. 1):S118, Aug. 1993; Program and Abstracts, Fifteenth Annual Meeting of the American Society for Bone & Mineral Research, Tampa, Florida, Sep. 18–22, 1993.

*Cells and Materials,* Supplement 1, 1991, *The Aged Rat Model for Bone Biology Studies,* pp. 1–192.

de Winter FR and Steendijk R; *The effect of a low–calcium diet in lactating rats; observations on the rapid development and repair of osteoporosis; Calcif. Tiss. Res.;* vol. 17, 1975, pp. 303–316.

Dukes M, Chester R, Yarwood L and Wakeling AE; *Effects of a non–steroidal pure antioestrogen, ZM 189, 154, on oestrogen target organs of the rat including bones; Journal of Endocrinology,* vol. 141, 1994, pp. 335–341.

Fisher B, Constantino JP, Redmond CK, Fisher ER, Wickerham DL, Cronin WM, et al., *Endometrial cancer in tamoxifen–treated breat cancer patients: findings from the national surgical adjuvant breast and bowel project (NSABP) B–14; Journal of the National Cancer Institute,* vol. 86, No. 7, Apr. 6, 1994, pp. 527–537.

Fornander T et al., *Adjuvant tamoxifen in early breast cancer: occurrence of new primary cancers; The Lancet;* Jan. 21, 1989, pp. 117–120.

Furr BJA and Jordan VC; *The pharmacology and clinical uses of tamoxifen; Pharmac. Ther.,* vol. 25, 1984, pp. 127–205.

Gallagher A, Chambers TJ, and Tobias JH, *The estrogen antagonist ICI 182, 780 reduces cancellous bone volume in female rats; Endocrinology,* vol. 133, 1993, pp. 2787–2791.

Janssens JP, Billiet G, Bonte J, and De Loecker W, *Effects of daily anti–estrogen treatment on uterine growth and progesterone receptor concentrations in adult rat uterus; Anticancer Research,* vol. 4, 1984, pp. 157–162.

Jones, CD, Jevnikar MG, Pike AJ et al., *Antiestrogen. 2. Structure–Activity Studies in a Series of 3–Aroyl–2–arylbenzo[b]thiophene Derivatives leading to [6–Hydroxy–2–(4–hydroxyphenyl)benzo[b]thien–3–yl][4–[2–(1–piperidiny)ethoxy]–phenyl]methanone Hydrochloride (LY156758), a Remarkably Effective Estrogen Antagonist with Only Minimal Intrinsic Estrogenicity; J. Med. Chem.,* vol. 27, 1984, pp. 1057–1066.

Jordan VC, *Biochemical pharmacology of antiestrogen action; Pharmacological Reviews,* vol. 36, No. 4, 1984, pp. 245–275.

Jordan, VC, *Estrogen Antiestrogen action and Breast Cancer Therapy,* (excerpts), pp. 28–30, and 516–517, (date unknown).

Jordan VC and Gosden B, *Inhibition of the uterotropic activity of estrogens and antiestrogens by the short acting antiestrogen LY117018, Endocrinology,* vol. 113, No. 2, 1983, pp. 463–468.

Jordan VC, *The strategic use of antiestrogens to control the development and growth of breast cancer; Cancer Supplement,* vol. 70, No. 4, Aug. 15, 1992, pp. 977–982.

Kimmel, DB, *Animal models for in vivo experimentation in osteoporosis research; Osteoporosis;* Chapter 33, pp. 671–690, 1996.

Lindsay R et al., *Long–term prevention of postmenopausal osteoporosis by estrogen; The Lancet;* May 15, 1976, pp. 1038–1040.

Marcus R, *Secondary Forms of Osteoporosis; Disorders of Bone and Mineral Metabolism,* 1992, Chapter 38, pp. 889–904.

Miller MA, Katzenellenbogen BS, *Characterization and quantitation of antiestrogen binding sites in estrogen receptor–positive and –negative human breast cancer cell lines; Cancer Research,* vol. 43, Jul. 1983, pp. 3094–3100.

Miller SC, Shupe JG, Redd EH, Miller MA, and Omura TH, *Changes in bone mineral and bone formation rates during pregnancy and lactation in rats; Bone,* vol. 7, 1986, pp. 283–287.

Minne HW, Parvici S, Feldmann S, Zegler R, *Antiestrogen treatment produces bone loss in female rats; J. Bone Mineral Res.,* vol. 1, Supplement 1, Jun. 1986, Abstract 255.

Mitlak BH, Williams DC, Bryant HU, Paul DC, and Neer RM, *Intermittent administration of bovine PTH–(1–34) increases serum 1,25–Dihydroxyvitamin concentrations and spinal bone density in senile (23 month) rats; J. Bone and Min. Res.;* vol. 7, No. 5, 1992, pp. 479–484.

Parvici S, Minne HW, Bauss F. Ziegler R; *Antiestrogen treatment produces loss of bone mass as a side–effect in the rat; Acta Endocrinol;* vol. 108, Supplement 267, 1985, Abstract 187.

Prince RL et al. *Prevention of postmenopausal osteoporosis; New England Journal of Medicine;* vol. 325, No. 17, Oct. 24, 1991, pp. 1189–1195.

Sutherland RL, Murphy LC; *Mechanisms of oestrogen antagonism by nonsteroidal antioestrogens; Molecular and Cellular Endocrinology;* vol. 25, 1982, pp. 5–23.

Wakeling, AE, O'Connor KM, Newboult E, *Comparison of the biological effects of tamoxifen and a new antioestrogen (LY 117018) on the immature rat uterus, J. Endocr.,* vol. 99, 1983, pp. 447–453.

Raloxifene/Trioxifene Combined Biblio (eff Jun. 23, 1993).

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.*

* cited by examiner

METHODS OF USE FOR INHIBITING BONE LOSS AND LOWERING SERUM CHOLESTEROL

Matter enclosed in heavy brackets [ ] appears in the original patent but forms no part of this reissue specification; matter printed in italics indicates the additions made by reissue.

FIELD OF THE INVENTION

This invention relates to methods for inhibiting bone loss and lowering serum cholesterol using low dosage amounts of particular 2-phenyl-3-aroylbenzothiophenes.

BACKGROUND OF THE INVENTION

I. Bone Loss

The current major disease or conditions of bone which are of public concern include post-menopausal osteoporosis, ovariectomy patients, senile osteoporosis, patients undergoing long-term treatment of corticosteroids, side effects from glucocorticoid or steroid treatment, patients suffering from Cushing's syndrome, gonadal dysgensis, periarticular erosions in rheumatoid arthritis, osteoarthritis, Paget's disease, osteohalisteresis, osteomalacia, hypercalcemia of malignancy, osteopenia due to bone metastases, periodontal disease, and hyperparathyroidism. All of these conditions are characterized by bone loss, resulting from an imbalance between the degradation of bone (bone resorption) and the formation of new healthy bone. This turnover of bone continues normally throughout life and is the mechanism by which bone regenerates. However, the conditions stated above will tip the balance towards bone loss such that the amount of bone resorbed is inadequately replaced with new bone, resulting in net bone loss.

One of the most common bone disorders is post-menopausal osteoporosis which affects an estimated 20 to 25 million women in the United States alone. Women after menopause experience an increase in the rate of bone turnover with resulting net loss of bone, as circulating estrogen levels decrease. The rate of bone turnover differs between bones and is highest in sites enriched with trabecular bone, such as the vertebrae and the femoral head. The potential for bone loss at these sites immediately following menopause is 4–5% per year. The resulting decrease in bone mass and enlargement of bone spaces leads to increased fracture risk, as the mechanical integrity of bone deteriorates rapidly.

At present, there are 20 million people with detectable vertebral fractures due to osteoporosis and 250,000 hip fractures per year attributable to osteoporosis in the U.S. The latter case is associated with a 12% mortality rate within the first two years and 30% of the patients will require nursing home care after the fracture. Therefore, bone disorders are characterized by a noticeable mortality rate, a considerable decrease in the survivor's quality of life, and a significant financial burden to families.

Essentially all of the conditions listed above would benefit from treatment with agents which inhibit bone resorption. Bone resorption proceeds by the activity of specialized cells called osteoclasts. Osteoclasts are unique in their ability to resorb both the hydroxyapatite mineral and organic matrix of bone. They are identical with the cartilage resorbing cells, previously termed chondroclasts. It is for this reason that potent inhibitors of osteoclastic bone resorption will also inhibit the cell-mediated degradation of cartilage observed in rheumatoid arthritis and osteoarthritis.

Therapeutic treatments to impede net bone loss include the use of estrogens. Estrogens have been shown clearly to arrest the bone loss observed after menopause and limit the progression of osteoporosis; but patient compliance has been poor because of estrogen side-effects. These side effects include resumption of menses, mastodynia, increase in the risk of uterine cancer, and possibly an increase in the risk of breast cancer.

Alternatively, calcitonin has been used to treat osteoporotic patients. Salmon calcitonin has been shown to directly inhibit the resorption activity of mammalian osteoclasts and is widely prescribed in Italy and Japan. However, calcitonins are prohibitively expensive to many and appear to be short-lived in efficacy. That is, osteoclasts are able to "escape" calcitonin inhibition of resorption by down-regulating calcitonin receptors. Therefore, recent clinical data suggest that chronic treatment with calcitonin may not have long term effectiveness in arresting the post-menopausal loss of bone.

II. Serum Cholesterol

All mammalian cells require cholesterol as a structural component off their cell membranes and for non-sterol end products. Cholesterol is also required for steroid hormone synthesis. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins have been demonstrated to be a major contributing factor in the development and progression of atherosclerosis.

In mammals, serum lipoprotein is composed of cholesterol together with cholesteryl esters, triglycerides, phospholipids and apoproteins. Serum or plasma lipoprotein is comprised of several fractions. The major fractions or classes of plasma lipoproteins are very low density lipoprotein (VLDL), low density lipoprotein (LDL), intermediate density lipoprotein (IDL), and high density lipoprotein (HDL). These classes differ from one another in size, density and in the relative proportions of triglycerides and cholesteryl esters in the core, and in the nature of the apoproteins on the surface.

In mammals, serum cholesterol is derived from exogenous dietary sources as well as through endogenous synthesis. Endogeneous synthesis of cholesterol involves a complex set of enzyme-catalyzed reactions and regulatory mechanisms generally termed the mevalonate pathway. Cells face a complex problem in regulating mevalonate synthesis because cholesterol, the bulk end product of mevalonate metabolism, is derived from plasma low density lipoprotein which enters the cell by receptor-mediated endocytosis, as well as from synthesis within the cell. Each cell must balance these external and internal sources so as to sustain mevalonate synthesis while avoiding sterol over accumulation. This balance is achieved through feedback regulation of at least two sequential enzymes in mevalonate synthesis, 3-hydroxy-3-methylglutaryl coenzyme A (HMG-CoA) synthase and HMG-CoA reductase and also of LDL receptors. In the absence of LDL, mammalian cells maintain high activities of the two enzymes, thereby synthesizing mevalonate for [product:ion] *production* of cholesterol as well as the non-sterol products. When LDL is present, from exogenous sources, HMG-CoA synthase and reductase activity is repressed and the cells produce smaller amounts of mevalonate for the non-sterol end products.

Abundant evidence indicates that treatment of hyperlipoproteinemia will diminish or prevent atherosclerotic complications. In addition to a diet that maintains a normal body weight and minimizes concentrations of lipids in plasma, therapeutic Strategies include elimination of factors that exacerbate hyperlipoproteinemia and the administration of therapeutic agents that lower plasma concentrations of lipoproteins, either by diminishing the production of lipoproteins or by enhancing the efficiency of their removal from plasma.

The most promising class of drugs currently available for the treatment of hypercholesterolemia act by inhibiting HMG-CoA reductase, the rate-limiting enzyme of endogenous cholesterol synthesis. Drugs of this class competitively inhibit the activity of the enzyme. Eventually, this lowers the endogenous synthesis of cholesterol and, by normal homeostatic mechanisms, plasma cholesterol is taken up by LDL receptors to restore the intracellular cholesterol balance.

Relative to other cells in the body, liver cells play a critical role in maintaining serum cholesterol homeostasis by both releasing precursors of LDL and through receptor mediated LDL uptake from the serum. In both man and animal models an inverse correlation appears to exist between liver LDL receptors and LDL-associated serum cholesterol levels. In general, higher hepatocyte receptor numbers result in lower LDL-associated serum cholesterol levels. Cholesterol released into hepatocytes can be stored as cholesterol esters, converted into bile acids and released into the bile duct, or enter into an oxycholesterol pool. It [ms] *is* this oxycholesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element, appears to confer this sterol end product repression. This element has been extensively studied (Brown, Goldstein and Russell, U.S. Pat. Nos. 4,745,060 and 4,935,363) and appears to consist of a 16 base pair sequence that occurs 5' of the LDL receptor coding region. The sterol response element can be inserted into genes that normally do not respond to cholesterol, conferring sterol end product repression on the chimeric gene. The exact mechanism of this repression is not understood. There is, however, abundant evidence that polar intermediates in cholesterol biosynthesis and naturally occurring as well as synthetic hydroxysterols repress genes containing the sterol response element.

It has been suggested that a hydroxycholesterol binding protein serves as a receptor. When the receptor is bound to an oxysterol it acts on the sterol response element to control transcription through a mechanism that is similar to the action of members of the steroid hormone receptor super gene family.

In populations where coronary heart disease is a major health problem, the incidence of the disease is markedly lower in women than in men. This is particularly true in younger age groups, such as men and women between 35 and 44 years of age.

Generally, plasma lipoprotein metabolism is influenced by the circulating concentrations of gonadal steroids. Changes in serum estrogen and androgen concentrations, resulting from alterations in gonadal status or from the administration of exogenous gonadal steroids are associated with changes in serum lipoprotein levels. The changes effected by estrogens and androgens generally support the proposition that sex differences in lipoproteins are due to hormonal differences between men and women.

The generally accepted relationship between gonadal steroids and plasma lipoproteins is that androgens lower HDL concentrations and increase LDL, thus contributing to the low HDL and high LDL levels observed in men when compared to women. Estrogens are held to have opposite effects on lipoproteins: that is HDL is raised and LDL is lowered. These sex steroid-induced differences in lipoprotein concentrations are thought to contribute to the lower incidence of cardiovascular disease in women compared to men. After the menopause, the protective effect of estrogens in women is lost and the incidence of cardiovascular disease increases towards the male levels. Postmenopausal women who take estrogens generally have lower rates of cardiovascular disease than women of a similar age who do not. Estrogen, particularly when taken orally, lowers plasma levels of LDL and raises those of HDL.

The mechanisms by which estrogen lowers levels of LDL and raises those of HDL are not known. In general, changes in the plasma concentration of a lipoprotein result from changes in the rate of its synthesis or the rate of its catabolism. For example, estrogen may lower LDL levels by increasing the clearance of LDL from plasma, since estrogen increases the number of hepatic LDL receptors in animals.

Although estrogens have beneficial effects on serum LDL, given even at very low levels, long-term estrogen therapy has been implicated in a variety of disorders, including an increase in the risk of uterine cancer and possibly breast cancer, causing many women to avoid this treatment. Recently suggested therapeutic regimens, which seek to lessen the cancer risk, such as administering combinations of progestogen and estrogen, cause the patient to experience regular bleeding, which is unacceptable to most older women. Furthermore, combining progesterone with estrogen seems to blunt the serum cholesterol lowering effects of estrogen. Concerns over the significant undesirable effects associated with estrogen therapy, support the need to develop alternative therapies for hypercholesterolemia that generates the desirable effects on serum LDL but does not cause undesirable effects.

Attempts to fill this need by the use of compounds commonly known as antiestrogens, which interact with the estrogen receptor and/or bind what has been termed the antiestrogen binding site (AEBS), have had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors such as the uterus. Therefore some antiestrogens, such as tamoxifen, are subject to some of the same adverse effects associated with estrogen therapy.

SUMMARY OF THE INVENTION

The invention provides a method of inhibiting bone resorption and bone loss comprising administering to a human in need thereof a compound of the formula (I)

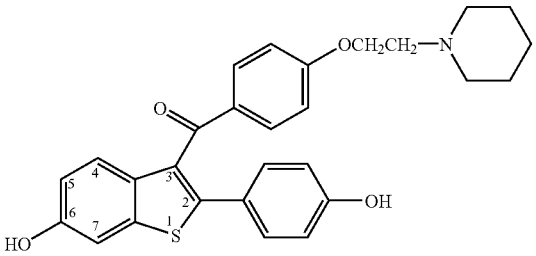

and pharmaceutically acceptable salts and solvates thereof, in an amount of about 50 to about 150 mg/day.

The invention also encompasses a method for lowering serum cholesterol comprising administering a compound of formula I in an amount of about 50 to about 150 mg/day.

The invention also [encompases] *encompasses* pharmaceutical formulations in dosage unit form, comprising, per dosage with an amount of about 50 to about 150 mg of a compound of formula I.

DESCRIPTION OF THE INVENTION

The current invention concerns the discovery that compounds of formula I are useful for lowering serum cholesterol levels and inhibiting bone resorption and bone loss at dosages of about 50 to about 150 mg/day. The methods provided by this invention are practiced by administering to a human in need thereof a dose of a compound of formula I or a pharmaceutically acceptable salt or solvate thereof in the amount of about 50 to about 150 mg/day, to lower serum cholesterol level, or inhibit bone loss or resorption.

The term "inhibit" is defined to include its generally accepted meaning which includes preventing, prohibiting, restraining, and slowing, stopping or reversing progression, or severity, and holding in check and/or treating existing characteristics. The present method includes both medical therapeutic and/or prophylactic treatment, as appropriate.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and are well suited to formulation as sustained release dosage forms and the like.

The method of the present invention is useful in men as well as women. The substantial absence of estrogenic response should allow men to employ the method of the present invention without evidencing the feminizing response of estrogen or estrogen agonists such as gynecomastia. Preferably, however, the methods of the present invention are useful in women, more preferably estrogen deficient women.

The 2-phenyl-3-aroylbenzothiophene compounds that are the active component in the methods of this invention were first developed by C. David Jones and Tulio Suarez as anti-fertility agents (U.S. Pat. No. 4,133,814, issued Jan. 9, 1979). Certain compounds in the group were found to be useful in suppressing the growth of mammary tumors.

Jones later found a group of related compounds to be useful for antiestrogen and antiandrogen therapy, especially in the treatment of mammary and prostatic tumors (U.S. Pat. No. 4,418,068, issued Nov. 29, 1983). One of these compounds, the hydrochloride salt form of the compound of formula I, was clinically tested for a brief time for the treatment of breast cancer. That compound is called raloxifene, formerly keoxifene.

Raloxifene is currently undergoing human clinical trials for use in [osteoporsis] *osteoporosis* and lipid lowering. Draper et al. ("Effects of Raloxifene on Biochemical Markers of Bone and Lipid Metabolism in Healthy Post-Menopausal Women," Fourth International Symposium on Osteoporosis, Hong Kong, Mar. 29, 1993) discussed certain positive findings of raloxifene's usefulness in inhibiting bone resorption and lowering serum cholesterol. The dosages tested were 200 mg/day and 600 mg/day. [As evidenced by EPO Publication EP-A-584952, published Mar. 2, 1994, (corresponding to] U.S. application Ser. No. 07/920,933 filed Jul. 28, 1992 (docket X-7947)[)], *similarly lists* the preferred range [is listed] as 200 mg to 600 mg/day. While this dosing range of 200–600 mg/day does provide sufficient response and is pharmaceutically acceptable it has now been found that a lower dosage range of raloxifene of about 50 mg/day to about 150 mg/day surprisingly results in providing equivalent benefits as compared to the higher range.

Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally or intravaginaly, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The hydroxyl groups of the starting compound are protected, the three position is acylated, and the product deprotected to form the formula I compounds. Examples of the preparation of such compounds are provided in the U.S. patents discussed above.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the likes. The formulations can be so constituted that they release the active ingredient only or preferably in a particular part of the intestinal tract, possibly over a period of time. The coatings, envelopes, and protective matrices may be made, for example, from polymeric substances or waxes.

The dosage range for the invention is about 50 to about 150 mg/day, and preferably 60 to 150 mg/day, and most preferably 60 to 100 mg/day. Particular dosages within the range of the invention were 50, 55, 60, 65, 70, 75, 80, 85, 90, 95, 100, 105, 110, 115, 120, 125, 130, 135, 140, 145, and 150 mg/day.

The compositions are preferably formulated in a unit dosage form each dosage containing about 50 to about 150 mg, and more preferably the amounts listed above. The term "unit dosage form" refers to physically discrete units, such as tablets and capsules, suitable as unitary dosages, particularly as unitary daily dosages, for human subjects and other mammals, each unit containing a predetermined quantity of active material calculated to produce the desired therapeutic effect, in association with a suitable pharmaceutical excipient.

The term or period of time of administration to a human subject of the dosage of about 50 to about 150 mg/day will vary depending upon severity of the condition, patient health, and related factors which will be decided upon by the attending physician. A course of treatment is expected to be at least for a period of six months, more normally at least one year, and [preferrably] *preferably* on a continual basis.

Examples of formulations using the dosage range follow:

| Formulations | |
|---|---|
| Ingredient | Quantity (mg/capsule) |
| Formulation 1: Gelatin Capsules | |
| Hard gelatin capsules are prepared using the following: | |
| Raloxifene | 50–150 |
| Starch, NF | 0–650 |
| Starch flowable powder | 0–650 |
| Silicone fluid 350 centistokes | 0–15 |
| The ingredients are blended, passed through a No. 45 mesh U.S. sieve, and filled into hard gelatin capsules. | |
| Examples of capsule formulations include those shown below: | |
| Formulation 2: Raloxifene capsule | |
| Raloxifene | 60 |
| Starch, NF | 112 |
| Starch flowable powder | 225.3 |
| Silicone fluid 350 centistokes | 1.7 |
| Formulation 3: Raloxifene capsule | |
| Raloxifene | 75 |
| Starch, NF | 108 |
| Starch flowable powder | 225.3 |
| Silicone fluid 350 centistokes | 1.7 |
| Formulation 4: Raloxifene capsule | |
| Raloxifene | 100 |
| Starch, NF | 103 |
| Starch flowable powder | 225.3 |
| Silicone fluid 350 centistokes | 1.7 |
| Formulation 5: Raloxifene capsule | |
| Raloxifene | 125 |
| Starch, NF | 150 |
| Starch flowable powder | 397 |
| Silicone fluid 350 centistokes | 3.0 |

-continued

| Formulations | |
|---|---|
| Ingredient | Quantity (mg/capsule) |
| Formulation 6: Raloxifene capsule | |
| Raloxifene | 150 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Tablets | |
|---|---|
| Ingredient | Quantity (mg/tablet) |
| Formulation 7: | |
| Raloxifene | 60 |
| Cellulose, microcrystalline | 0–650 |
| Silicon dioxide, fumed | 0–650 |
| Stearate acid | 0–15 |
| Formulation 8: | |
| Raloxifene | 75 |
| Cellulose, microcrystalline | 0–650 |
| Silicon dioxide, fumed | 0–650 |
| Stearate acid | 0–15 |
| Formulation 9: | |
| Raloxifene | 100 |
| Cellulose, microcrystalline | 0–650 |
| Silicon dioxide, fumed | 0–650 |
| Stearate acid | 0–15 |
| Formulation 10: | |
| Raloxifene | 125 |
| Cellulose, microcrystalline | 0–650 |
| Silicon dioxide, fumed | 0–650 |
| Stearate acid | 0–15 |
| Formulation 11: | |
| Raloxifene | 150 |
| Cellulose, microcrystalline | 0–650 |
| Silicon dioxide, fumed | 0–650 |
| Stearate acid | 0–15 |

The components are blended and compressed to form tablets.

Alternatively, tablets each containing 50 to 150 mg of active ingredient are made up as follows:

| Tablets | |
|---|---|
| Ingredient | Quantity (mg/tablet) |
| Formulation 12: | |
| Raloxifene | 60 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

-continued

| Tablets | |
|---|---|
| Ingredient | Quantity (mg/tablet) |
| Formulation 13: | |
| Raloxifene | 75 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |
| Formulation 14: | |
| Raloxifene | 100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |
| Formulation 15: | |
| Raloxifene | 125 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |
| Formulation 16: | |
| Raloxifene | 150 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 50–150 mg of medicament per 5 mL dose are made as follows:

| Suspensions | |
|---|---|
| Ingredient | Quantity (mg/5 ml) |
| Formulation 17: | |
| Raloxifene | 60 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

-continued

| Suspensions | |
|---|---|
| Ingredient | Quantity (mg/5 ml) |
| Formulation 18: | |
| Raloxifene | 75 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |
| Formulation 19: | |
| Raloxifene | 100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |
| Formulation 20: | |
| Raloxifene | 125 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |
| Formulation 21: | |
| Raloxifene | 150 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted[:] with some of the water and added, with stirring. Sufficient water is then added to produce the required volume.

The following examples illustrate the preparation of the compounds used in the invention.

EXAMPLE 1

6-hydroxy-2-(4-hydroxyphenyl)-3-[4-(2-piperidinoethoxy)benzoyl]benzo[b]thiophene A 4 g. portion of 6-methanesulfonyloxy-2-(4-methanesulfonyloxyphenyl)-3-[4-(2-piperidinoethoxy)-benzoyl]benzo[b]thiophene, hydrochloride, was combined with 100 ml. of denatured alcohol and 10 ml. of 5 N sodium hydroxide, and stirred under reflux for 1.5 hours under a nitrogen atmosphere. The reaction mixture was then evaporated to dryness under vacuum, and the residue was dissolved in 200 ml. of water and washed with 300 ml. of diethyl ether. The water layer was degassed under vacuum, and then nitrogen was bubbled through it to remove all traces of ether. The mixture Was then acidified with 1 N hydrochloric acid, and then made basic with excess sodium bicarbonate. The precipitate Was collected by filtration and washed with cold water to obtain 2.4 g. of crude product. It was purified on a 2×30 cm. column of silica gel, eluting first with 700 ml. of 55 methanol in chloroform, followed by 1 liter of 10% methanol in chloroform. The impurities came off first, and the product-containing fractions were combined and evaporated under vacuum to obtain 1.78 g. of yellow oil. The oil was dissolved in 6 m. of acetone, seeded and chilled in a freezer to obtain 1.2 g. of purified product, m.p. 143°–147° C. The identity of the product was confirmed as follows:

nmr spectrum (100 mHz in dmso-$d_6$)δ1.20–1.65(6H, m, $N(CH_2CH_2)_2CH_2$); 2.30–2.45 (4H, m, $N(CH_2CH_2)_2CH_2$); 2.60 (2H, t, J=6 Hz, $OCH_2CH_2N$); 4.06(2H, t, J=6Hz, $OCH_2CH_2N$); 6.68 (2H, d, J=9H, aromatic o to OH); 6.85 (1H, q, $J_{H4-H5}$=9 Hz, $J_{H5-H7}$=2 Hz, H5 of benzothiophene ring); 6.90(2H, d, J=9 Hz, aromatic o to $OCH_2CH_2N$); 7.18 (2H, d, J=9 Hz, aromatic m to OH); 7.25 (1H, d, J=9z, H4 of benzothiophene ring); 7.66 (2H, d, J=9 Hz, aromatic o to CO); 9.72(2H, broad s, OH). Ultraviolet spectrum in ethanol; $\lambda_{max}$ (ε): 290 nm. (34,000). Electron impact mass Spectrum $M_f$ at m/e 473.

EXAMPLE 2

6-hydroxy-2-(4-hydoxyphenyl)-3-[4-(2-piperidinoethoxy)benzoyl]benzo[b]thiophene A 3.6 g. portion of 6-methanesulfonyloxy-2-(4-methanesulfonyloxyphenyl)-3-[4-(2-piperidinoethoxy)-benzoyl]benzo[b]thiophene was dissolved in 100 ml. of tetrahydrofuran and 40 ml. of methanol, and 10 ml. of 5 N sodium hydroxide was added. The mixture was stirred for 16 hours at ambient temperature, and was then worked up by the procedure of Example 1 above to obtain 3.5 g of a yellow solid. The impure product was purified by column chromatography on silica gel, eluting with a gradient solvent from 5% methane in chloroform to 30% methanol in chloroform. The product-containing fractions were evaporated to obtain 1.85 g. of oily product, which was recrystallized from acetone to obtain 1.25 g. of purified product, m.p. 141°–144° C.

EXAMPLE 3

6-hydroxy-2-(4-hydroxyphenyl)-3[4-(2-piperidinoethoxy)benzoyl]benzo[b]thiophene, hydrochloride Under a nitrogen blanket, a mixture of 3 g. of 4-(2-piperidinoethoxy) benzoic acid, hydrochloride, 2 drops of dimethylformamide, 2.5 ml. of thionyl chloride and 40 ml. of chlorobenzene was heated at 70°–75° C. for about one hour. The excess thionyl chloride and 15–20 ml. of solvent were then distilled off. The remaining suspension was cooled to ambient temperature, and to it were added 100 ml. of dichloromethane, 2.7 g. of 6-methoxy-2-(4-methoxyphenyl)benzo[b]thiophene and 10 g. of aluminum chloride. The solution was stirred for about one hour, 7.5 ml. of ethanethiol was added, and the mixture was stirred for 45 minutes more. Then 40 ml. of tetrahydrofuran was added, followed by 15 ml. of 20% hydrochloric acid, with an exotherm to reflux. Fifty ml. of water and 25 ml. of saturated aqueous sodium chloride were added. The mixture was stirred and allowed to cool to ambient temperature. The precipitate was collected by filtration and washed successively with 30 ml of water, 40 ml of 25% aqueous tetrahydrofuran, and 35 ml. of water. The solids were then dried at 40° C. under vacuum to obtain 5.05 g. of product, which was identified by nmr.

δ1.7(6H, m, $N(CH_2CH_2)_2CH_2$); 2.6–3.1 (2H, m, NCH2); 3.5–4.1 (4H, m, $NCH_2$); 4.4 (2H, m, $OCH_2$); 6.6–7.4 (9H, m, aromatic); 7.7 (2H, d, aromatic o to CO); 9.8(2H, m, OH).

Test Results

An 8-week parallel, double-blind, placebo study in approximately 160 healthy post-menopausal women was completed. The doses of raloxifene used in this study were 10, 50, and 200 mg. The 10 mg dose had no significant activity with either bone marker. (See Table I) Because of development over time seen with many bone markers, a raloxifene dose of 50 mg/day will likely be fully active when evaluated during a study of longer duration.

TABLE I

Baseline Values and Mean (±SEM) Group Changes from Baseline to Endpoint in Markers of Bone Metabolism (GGGC)

| Marker | Placebo (n = 42) | Raloxifene 10 mg (n = 42) | Raloxifene 50 mg (n = 42) | Raloxifene 200 mg (n = 41) |
|---|---|---|---|---|
| | Serum alkaline phosphatase (U/L) | | | |
| Baseline | 77.31 (±3.53) | 78.71 (±3.12) | 73.86 (±2.69) | 79.07 (±2.77) |
| Change | −1.10 (±2.08) | 0.21 (±1.56) | −4.78 (±1.52) | −5.93* (±1.48) |
| | Serum osteocalcin (ng/mL) | | | |
| Baseline | 3.94 (±0.21) | 3.86 (±0.19) | 3.65 (±0.21) | 4.21 (±0.21) |
| Change | −0.63 (±0.16) | −0.27 (±0.13) | −0.81 (±0.15) | −1.21* (±0.18) |

Abbreviations: n = greatest number of subjects tested for any one marker; SEM = standard error of the mean.
*Statistically significantly ($p < 0.051$) different from placebo (two-tailed comparison).

Serum lipid levels were affected by raloxifene doses of 50 and 200 mg (Table II). Decreases in LDL cholesterol were observed in raloxifene[-] treated subjects at 50 mg with a comparable decrease in the 200 mg patients. Raloxifene-treated subjects showed no changes in HDL levels. Statistically significant decreases in HDL:LDL ratios and the total serum cholesterol levels were observed in raloxifene-treated subjects at both the 50 and 200 mg doses.

TABLE II

Baseline Values and Mean (±SEM) Group Changes from Baseline to Endpoint in Serum Lipids (GGGC)

| Variable | Placebo (n = 42) | Raloxifene 10 mg (n = 42) | Raloxifene 50 mg (n = 42) | Raloxifene 200 mg (n = 41) |
|---|---|---|---|---|
| | LDL-C (mmol/L) | | | |
| Baseline | 3.67 (±0.11) | 4.11# (±0.17) | 3.55 (±0.16) | 3.68 (±0.13) |
| Change | 0.02 (±0.08) | 0.05 (±0.10) | −0.23* (±0.06) | −0.17 (±0.07) |
| | HDL-C (mmol/L) | | | |
| Baseline | 1.41 (±0.06) | 1.41 (±0.06) | 1.35 (±0.05) | 1.32 (±0.05) |
| Change | −0.03 (±0.03) | 0.01 (±0.02) | 0.04 (±0.02) | 0.02 (±0.02) |
| | HDL-C:LDL-C ratio | | | |
| Baseline | 0.40 (±0.02) | 0.37 (±0.03) | 0.42 (±0.03) | 0.38 (±0.02) |
| Change | −0.01 (±0.01) | 0.00 (±0.01) | 0.03* (±0.01) | 0.03* (±0.01) |
| | Toal cholesterol (mmol/L) | | | |
| Baseline | 5.69 (±0.12) | 6.18# (±0.19) | 5.82 (±0.21) | 5.71 (±0.14) |

TABLE II-continued

Baseline Values and Mean (±SEM) Group Changes from Baseline to Endpoint in Serum Lipids (GGGC)

| Variable | Placebo (n = 42) | Raloxifene 10 mg (n = 42) | Raloxifene 50 mg (n = 42) | Raloxifene 200 mg (n = 41) |
|---|---|---|---|---|
| Change | 0.10 (±0.09) | 0.01 (±0.10) | −0.23* (±0.08) | −0.15 (±0.08) |

Abbreviations: LDL-C = low-density lipoprotein cholesterol; HDL-C = high-density lipoprotein cholesterol; n = greatest number of subjects tested for any one marker; SEM = standard error of the mean.
#Statistically significantly ($p < 0.050$) larger than all other treatments (two-tailed comparison).
*Statistically significantly ($p < 0.050$) different from placebo (two-tailed comparison).

I claim:

1. A method of inhibiting *post-menopausal* bone loss [or bone resorption] *in a post-menopausal woman in need of treatment to prevent or to treat post-menopausal osteoporosis* comprising administering to [a human] *said woman* in need [thereof] *of said treatment* a compound of formula I (I)

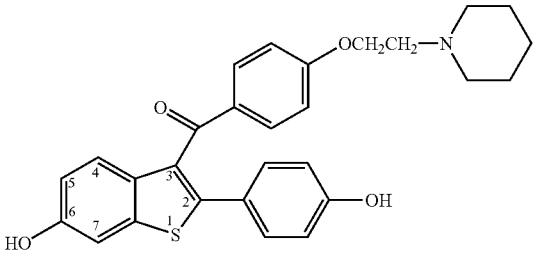

or a pharmaceutically acceptable salt or solvate thereof, in an amount of [about 50 to about 150] *55 to 65* mg/day.

2. A method of claim 1 wherein [the human] *said woman* has been diagnosed as suffering from *post-menopausal* osteoporosis.

[3. A method of claim 1 wherein the human is a post-menopausal female.]

[4. A method of claim 1 wherein the human is a male.]

5. A method of claim 1 wherein the compound is administered prophylactically.

[6. A method of claim 1 wherein the compound of formula I is administered in an amount of about 60 to about 150 mg/day.]

7. A method of claim 1 wherein the compound of formula I is administered in an amount of 60 mg/day.

8. A method of claim 1 wherein the compound of formula I is administered in an amount of [75] *55* mg/day.

9. A method of claim 1 wherein the compound of formula I is administered in an amount of [100] *65* mg/day.

[10. A method of claim 1 wherein the compound of formula I is administered in an amount of 125 mg/day.]

[11. A method of claim 1 wherein the compound of formula I is administered in an amount of 150 mg/day.]

12. A method of claim 1 [wherein the compound is the] *which comprises administering a* hydrochloride salt *of a compound of formula I.*

*13. A method of claim 12 wherein the hydrochloride salt is administered in an amount of 60 mg/day.*

*14. A method of preventing post-menopausal osteoporosis in a post-menopausal woman in need of treatment to prevent post-menopausal osteoporosis comprising administering to*

*said woman a hydrochloride salt of a compound of Formula I*
(I)
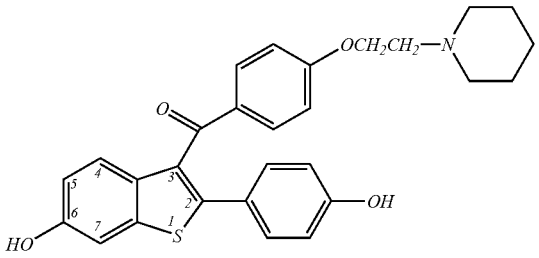
*in an amount of 60 mg/day.*
*15. A method of treating post-menopausal osteoporosis in a post-menopausal woman in need of treatment for post-menopausal osteoporosis comprising administering to said woman a hydrochloride salt of a compound of Formula I*
(I)
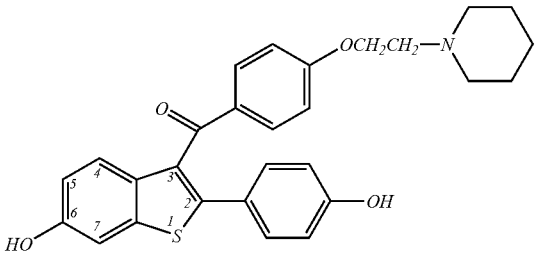
*in an amount of 60 mg/day.*
* * * * *